(12) United States Patent
Vinkers et al.

(10) Patent No.: US 10,504,379 B2
(45) Date of Patent: Dec. 10, 2019

(54) SYSTEM AND METHOD FOR GENERATING AN ADAPTIVE EMBODIED CONVERSATIONAL AGENT CONFIGURED TO PROVIDE INTERACTIVE VIRTUAL COACHING TO A SUBJECT

(71) Applicant: KONINKLIJKE PHILIPS N.V., Eindhoven (NL)

(72) Inventors: Charlotte Dorothea Wilhelmina Vinkers, Eindhoven (NL); Arlette Van Wissen, Culemborg (NL); Aart Tijmen Van Halteren, Geldrop (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 108 days.

(21) Appl. No.: 15/566,014

(22) PCT Filed: May 12, 2016

(86) PCT No.: PCT/IB2016/052721
§ 371 (c)(1),
(2) Date: Oct. 12, 2017

(87) PCT Pub. No.: WO2016/193839
PCT Pub. Date: Dec. 8, 2016

(65) Prior Publication Data
US 2018/0130372 A1 May 10, 2018

Related U.S. Application Data

(60) Provisional application No. 62/295,196, filed on Feb. 15, 2016, provisional application No. 62/170,424, filed on Jun. 3, 2015.

(51) Int. Cl.
*A63F 9/24* (2006.01)
*G09B 19/00* (2006.01)
(Continued)

(52) U.S. Cl.
CPC ......... *G09B 19/00* (2013.01); *G06F 19/3481* (2013.01); *G06N 3/006* (2013.01);
(Continued)

(58) Field of Classification Search
CPC ..... G06F 19/00; G06F 19/3418; G06N 3/006; G09B 19/0092; G16H 10/60; G16H 40/63; G16H 50/20
See application file for complete search history.

(56) References Cited

U.S. PATENT DOCUMENTS 6,605,038 B1 * 8/2003 Teller ............... A61B 5/411
600/300
2007/0166690 A1 7/2007 Johnson
(Continued)

FOREIGN PATENT DOCUMENTS

DE 102011052836 A1 2/2012
WO 2015021208 A1 2/2015

*Primary Examiner* — Steve Rowland

(57) ABSTRACT

The present disclosure pertains to a system configured to generate an adaptive embodied conversational agent to provide interactive virtual coaching to a subject. The system comprises a user interface, one or more hardware processors, and a display. The user interface is configured to obtain input information related to the subject. The one or more hardware processors are configured by machine-readable instructions to: determine a customized digital coaching plan for the subject; and generate visual and/or audio signals that convey the appearance and behavior of the adaptive embodied conversational agent based on the customized digital coaching plan, and/or based on a relationship parameter. The display is configured to receive the generated visual and/or audio signals and cause presentation of the adaptive embodied conversational agent on the display to provide the customized digital coaching plan to the subject interactively.

18 Claims, 5 Drawing Sheets

(51) Int. Cl.
| | | |
|---|---|---|
| *G06F 19/00* | (2018.01) | |
| *G16H 40/63* | (2018.01) | |
| *G16H 50/20* | (2018.01) | |
| *G16H 10/60* | (2018.01) | |
| *G06N 3/00* | (2006.01) | |
| *G09B 5/06* | (2006.01) | |
| *G09B 5/12* | (2006.01) | |
| *G09B 7/02* | (2006.01) | |
| *G09B 7/077* | (2006.01) | |

(52) U.S. Cl.
CPC ............... *G09B 5/065* (2013.01); *G09B 5/12* (2013.01); *G09B 7/02* (2013.01); *G09B 7/077* (2013.01); *G16H 10/60* (2018.01); *G16H 40/63* (2018.01); *G16H 50/20* (2018.01)

(56) References Cited

U.S. PATENT DOCUMENTS

| | | | |
|---|---|---|---|
| 2008/0262557 A1 | 10/2008 | Brown | |
| 2009/0089100 A1* | 4/2009 | Nenov | G06Q 50/22 705/3 |
| 2011/0053128 A1* | 3/2011 | Alman | A61B 5/0002 434/236 |
| 2012/0016678 A1* | 1/2012 | Gruber | G10L 15/22 704/275 |
| 2013/0046149 A1* | 2/2013 | Gettelman | A61B 5/744 600/301 |
| 2014/0074454 A1* | 3/2014 | Brown | G10L 15/08 704/9 |
| 2014/0088996 A1* | 3/2014 | Damani | G06F 19/3418 705/2 |
| 2014/0248595 A1* | 9/2014 | Crabtree | G09B 5/08 434/247 |
| 2014/0356822 A1 | 12/2014 | Hoque et al. | |
| 2015/0004578 A1 | 1/2015 | Gilley et al. | |
| 2015/0356261 A1* | 12/2015 | Brust | G06F 3/0481 705/2 |
| 2015/0371663 A1* | 12/2015 | Gustafson | G10L 15/265 704/270.1 |

* cited by examiner

| Interaction | Speech production | Intelligence | Appearance |
|---|---|---|---|
| Toch screen input | Pre-recorded speech | Knowledge base | 2+D |
| Typed input | Generate synthetic speech | Consistent, coherent, clear conversations | Upload picture of real person |
| Speech recognition | Synchronization with animation | Dynamic conversation based on user input | Change static characteristics |
| User- and agent-initiated conversation | Variability in content expression | Access to eCP data | Emotional expressions |
| Non-verbal behavior recognition | Variability in intonation | Learn from interactions | Movement head and posture |
| User-controlled settings | Variability of discourse patterns | Memory of past interactions | Variability in expressions |
| Interruption mechanism | Features of speech (pitch, accent, emotion) | Auto-connect to devices | Handle objects |
| Context recognition | | | Arms & hands, backgrounds |

FIG. 4

SYSTEM AND METHOD FOR GENERATING AN ADAPTIVE EMBODIED CONVERSATIONAL AGENT CONFIGURED TO PROVIDE INTERACTIVE VIRTUAL COACHING TO A SUBJECT

CROSS-REFERENCE TO PRIOR APPLICATIONS

This application is the U.S. National Phase application under 35 U.S.C. § 371 of International Application No. PCT/IB32016/052721, filed on 12 May 2016, which claims the benefit of U.S. Provisional Patent Application No. 62/170424, filed on 3 Jun. 2015 and 62/295196, filed on 15 Feb. 2016. These applications are hereby incorporated by reference herein.

BACKGROUND

1. Field

The present disclosure pertains to a system and method for generating a adaptive embodied conversational agent configured to provide interactive virtual coaching to a subject.

2. Description of the Related Art

Healthcare costs may increase in part due to disproportional consumption of healthcare resources by chronic patients. Providing supportive care to chronic patients in an outpatient setting may be complicated due to the fact that these patients need to self-manage their care in the environment which may have contributed to their condition in the first place. It is not uncommon for chronic patients to experience exacerbations of their condition once they return home, resulting in a subsequent readmission to a medical facility. Supporting these patients with a live human health coach has been found to be effective because of the psychological and physiological guidance and support provided. While feasible to provide live human coaching in the inpatient setting, many patients lack access to this level of supportive care in an outpatient and/or home setting.

SUMMARY

Accordingly, one or more aspects of the present disclosure relate to a system configured to generate an adaptive embodied conversational agent. The adaptive embodied conversational agent is configured to provide interactive virtual coaching to a subject. The system comprises: a user interface configured to obtain input information related to the subject. The information includes one or more of physiological information, behavior information, psychological information, or medical information. The system further comprises one or more hardware processors configured by machine-readable instructions to: determine a customized digital coaching plan for the subject, wherein the customized digital coaching plan is based on the information related to the subject; and generate digital (e.g., visual and/or audio) signals conveying information related to the adaptive embodied conversational agent based on the customized digital coaching plan, wherein the information related to the adaptive embodied conversational agent includes verbal behavioral characteristics and non-verbal characteristics of the adaptive embodied conversational agent. The system further comprises a display configured to receive the generated visual and/or audio signals (the signals generated by the one or more processors based on information captured by sensors etc. (described below)) and cause presentation of the adaptive embodied conversational agent on the display to provide the customized digital coaching plan to the subject interactively.

Another aspect of the present disclosure relates to a method for generating an adaptive embodied conversational agent configured to provide interactive virtual coaching to a subject with a system. The system comprises a user interface, one or more hardware processors, a display, and/or other components. The method comprises obtaining, with the user interface, input information related to the subject. The information includes one or more of physiological information, behavior information, psychological information, and/or medical information. The method further comprises determining, with the one or more hardware processors, a customized digital coaching plan for the subject. The customized digital coaching plan is based on the information related to the subject. The method further comprises generating, with the one or more hardware processors, visual and/or audio signals conveying information related to the adaptive embodied conversational agent based on the customized digital coaching plan. The information related to the adaptive embodied conversational agent includes verbal behavioral characteristics and non-verbal characteristics of the adaptive embodied conversational agent. The method further comprises receiving, with the display, the generated visual and/or audio signals and causing presentation of the adaptive embodied conversational agent on the display to provide the customized digital coaching plan to the subject interactively.

Still another aspect of present disclosure relates to a system configured to generate an adaptive embodied conversational agent configured to provide interactive virtual coaching to a subject. The system comprises means for obtaining input information related to the subject. The information includes one or more of physiological information, behavior information, psychological information, or medical information. The system further comprises means for determining a customized digital coaching plan for the subject. The customized digital coaching plan is based on the information related to the subject. The system further comprises means for generating visual and/or audio signals conveying information related to the adaptive embodied conversational agent based on the customized digital coaching plan. The information related to the adaptive embodied conversational agent includes verbal behavioral characteristics and non-verbal characteristics of the adaptive embodied conversational agent. The system further comprises means for receiving the generated visual and/or audio signals and causing presentation of the adaptive embodied conversational agent on the display to provide the customized digital coaching plan to the subject interactively.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

BRIEF DESCRIPTION OF THE DRAWINGS

FIG. 4 illustrates an example of features of the system in accordance with one or more implementations.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Health systems are looking for equally effective yet scalable alternatives to human health coaches, which can be provided in outpatient facilities, home, and/or other environments. To help provide supportive care to these patients and break the readmission cycle, it has been suggested that virtual health coaching at home would benefit these patients by providing cost-effective, personalized, and dynamically adaptive coaching like the human support they receive in the inpatient and/or outpatient settings. However, obtaining voluntary patient engagement and compliance when provided by a virtual health coach remains a challenge.

Figure 1:
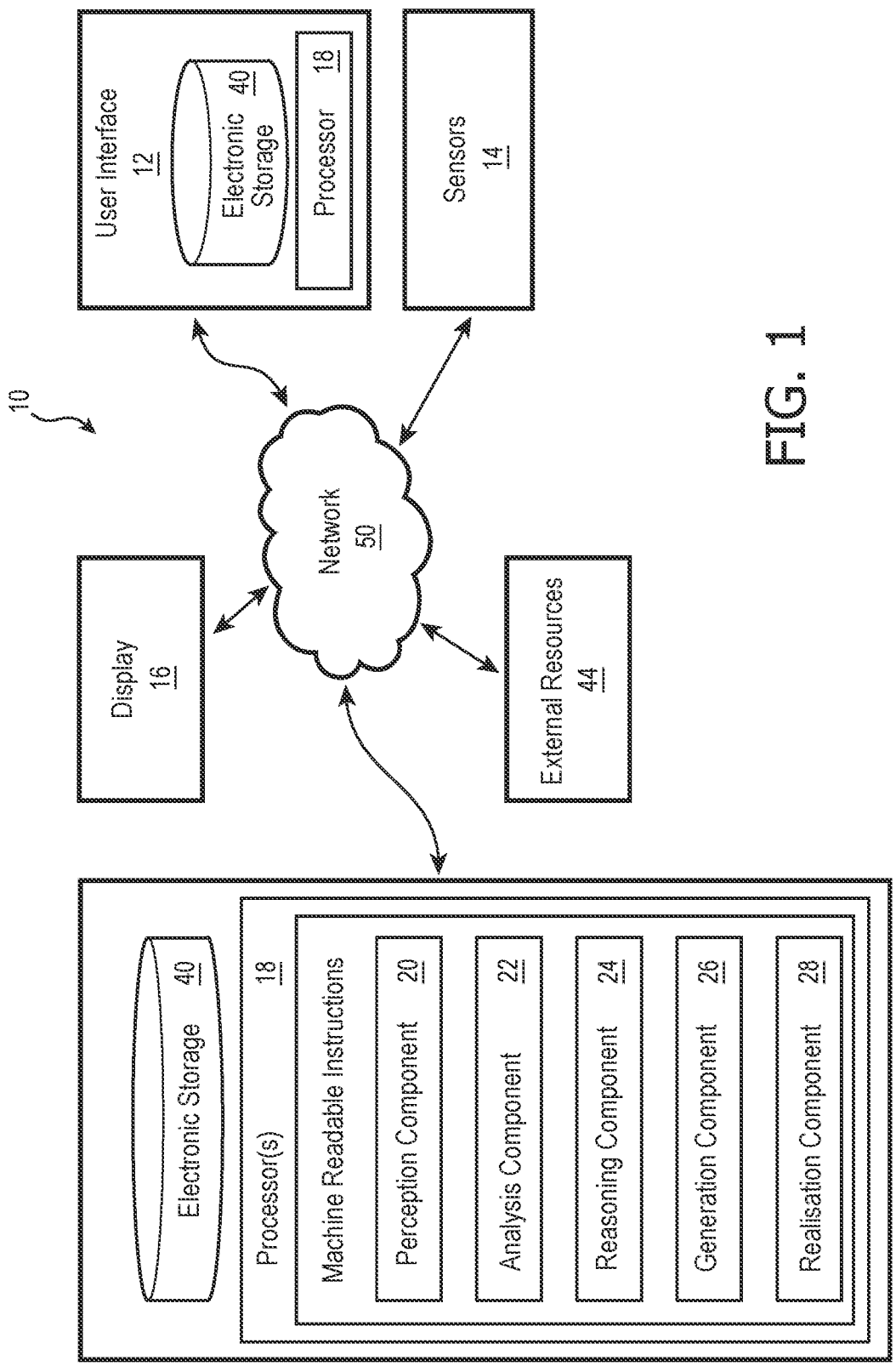
FIG. 1 is a schematic illustration of a system for generating a adaptive embodied conversational agent to provide interactive virtual coaching to a subject in accordance with one or more implementations.

FIG. 1 is a schematic illustration of a system 10 configured to generate an adaptive embodied conversational agent. The adaptive embodied conversational agent is configured to provide interactive virtual coaching that is adapted to a subject (e.g., medical patient, mental patient, and/or other subjects). The adaptive embodied conversational agent is a machine generated character, represented graphically with a virtual body, configured to interact with a user of the system in verbal and non-verbal manners (e.g., speech, hand gestures, facial and body expressions, etc.). The adaptive embodied conversational agent is configured to respond to verbal and non-verbal communications from the user in ways similar of that of face to face conversation between humans (by means of speech recognition, non-verbal behavior recognition, etc.). In current clinical practice, human health coaching is often limited or not available to all patients, and if available, is labor-intensive, costly, and as such less scalable compared to automated forms of health coaching. Additionally, human health coaching may be limited to in-clinic visits, or to arranged home visits by professionals. This limits accessibility to coaching whenever the patient requires support. The present system addresses the above shortcomings by providing a system for generating an adaptive embodied conversational agent configured to provide interactive virtual coaching to a medical and/or mental patient. This system will potentially increase the breadth and depth of the outreach and interaction with a patient population.

In some embodiments, system 10 comprises a user interface 12, one or more sensors 14, a display 16, hardware processor(s) 18, electronic storage 40, external resources 44, and/or other components. One or more components of system 10 may be communicatively coupled via a network 50 and/or other coupling mechanisms.

Processor 18 is configured to provide information processing capabilities in system 10. As such, processor 18 may comprise one or more of a digital processor, an analog processor, and a digital circuit designed to process information, an analog circuit designed to process information, a state machine, and/or other mechanisms for electronically processing information. In some embodiments, processor 18 may comprise a plurality of processing units. These processing units may be physically located within the same device (e.g., a server), or processor 18 may represent processing functionality of a plurality of devices operating in coordination (e.g., a server; computing devices associated with a user, user interface 12, medical devices, devices that are part of external resources 44, and/or other devices.)

As shown in FIG. 1, processor 18 is configured via machine-readable instructions to execute one or more computer program components. The one or more computer program components may comprise one or more of a perception component 20, an analysis component 22, a reasoning component 24, a generation component 26, a realization component 28 and/or other components. Processor 18 may be configured to execute components 20, 22, 24, 26 and/or 28 by software; hardware; firmware; some combination of software, hardware, and/or firmware; and/or other mechanisms for configuring processing capabilities on processor 18.

It should be appreciated that although components 20, 22, 24, 26 and 28 are illustrated in FIG. 1 as being co-located within a single processing unit, in embodiments in which processor 18 comprises multiple processing units, one or more of components 20, 22, 24, 26 and/or 28 may be located remotely from the other components. The description of the functionality provided by the different components 20, 22, 24, 26 and/or 28 described below is for illustrative purposes, and is not intended to be limiting, as any of components 20, 22, 24, 26 and/or 28 may provide more or less functionality than is described. For example, one or more of components 20, 22, 24, 26 and/or 28 may be eliminated, and some or all of its functionality may be provided by other components 20, 22, 24, 26 and/or 28. As another example, processor 18 may be configured to execute one or more additional components that may perform some or all of the functionality attributed below to one of components 20, 22, 24, 26 and/or 28.

User interface 12 may be configured to obtain input information related to the subject by facilitating entry and/or selection of information by the subject, caregivers, and/or other users. For example, user interface 12 may be configured to display one or more views of a graphical user interface to a user (e.g., patient, caregiver, etc.) which facilitate entry and/or selection of information by the user. In some embodiments, user interface 12 refers to one or more user interfaces associated with one or more users. In some embodiments, user interface 12 is configured to facilitate entry and/or selection of information through a medical device, a sensor, a website, a mobile app, a bot through which text messages and/or emails are sent, and/or via other methods. In some embodiments, user interface 12 is configured to prompt the subject, caregivers, and/or other users to answer specific questions related to the subject medical conditions, physiological conditions, health, mood, and/or other questions.

User interface 12 is configured to receive information from and/or provide information to one or more users of system 10. User interface may be located in a personal computing device, a medical device, and/or other locations within or outside system 10. User interface 12 is configured to provide an interface between system 10 and the user. This enables data, cues, results, and/or instructions and any other communicable items, collectively referred to as "information," to be communicated between the user, processor 18, sensors 14, and/or other components of system 10. For example, recommendations, reviews, graphs, predictions, and/or other information may be communicated from system 10 to the user via user interface 12.

Examples of interface devices suitable for inclusion in user interface 12 comprise a graphical user interface, a display, a touchscreen, a keypad, buttons, switches, a keyboard, knobs, levers, speakers, a microphone, an indicator light, an audible alarm, a printer, a haptic feedback device, an optical scanner, a bar-code reader, a camera, and/or other interface devices. In some embodiments, user interface 12 comprises a plurality of separate interfaces. For example, user interface 12 may comprise a plurality of different interfaces associated with a plurality of computing devices associated with different caregivers; an interface that is part of a computing device associated with the user; processor 18, electronic storage 40, external resources 44, sensors 14, and/or other components of system 10; an interface included in a server that also includes processor 18 and/or electronic storage 40; and/or other interfaces. User interface 12 is configured such that a user may provide information to and receive information from system 10 via the individual ones of the plurality of user interfaces. In some embodiments, user interface 12 comprises at least one interface that is provided integrally with processor 18 and/or other components of system 10.

Display 16 is configured to receive generated visual and/or audio signals and cause presentation of the adaptive embodied conversational agent on the display. In some embodiments, display 16 may be configured to present the adaptive embodied conversational agent and/or other information. In some embodiments, display 16 is included in user interface 12. In some embodiment user interface 12 is display 16. In some embodiments, display 16 may comprise a graphical user interface, a display, a touchscreen, and/or other display devices. In some embodiments, display 16 may include subject monitors, nursing stations, mobile communications devices, subject information systems, and/or other graphic or electronic displays.

Sensors 14 are configured to generate output signals conveying information related to the subject. In some embodiments, sensors 14 may convey information related to verbal and non-verbal behavior of the subject. Sensors 14 may include audiovisual sensors, activity sensors, physiological sensors, and/or other sensors. In some embodiments, sensors 14 may be configured to transmit (e.g., wired or wirelessly) information directly to processors 18. Examples of such sensors may include a heart rate sensor, a blood pressure sensor/monitor, a weight scale, motion sensors, an optical sensor, a video sensor, an audio sensor, a color sensor, a blood glucose monitor, a blood oxygen saturation monitor, a hydration monitor, a skin/body temperature thermometer, a respiration monitor, electroencephalogram (EEG) electrodes, bed sensors, accelerometers, activity sensors/trackers, a GPS sensor, and/or other sensors. These examples should not be considered limiting. Sensors 14 are configured to generate any output signals conveying information related to the subject that allows system 10 to function as described herein. In some embodiments, sensors 14 may be disposed in a plurality of locations within or outside of system 10. For example, sensors 14 may be on the subject, coupled with the user interface 12, located in a medical device used by the subject, positioned to point at the subject (e.g., a video camera), and/or in other locations within or outside of system 10. In some embodiments, information related to the subject may be obtained through a combination of user input, user selection, sensor outputs, and/or other methods.

Perception component 20 is configured to obtain information related to the subject. Information related to the subject may include one or more of identifying information, physiological information, behavior information, psychological information, medical information, and/or other information related to the subject. For example, identifying information may include the subject's name, age, gender, and/or other identifying information. Examples of physiological information may include heart rate, blood pressure, weight, pulse rate, blood chemistry, blood oxygen saturation, blood glucose level, hydration information, respiration rate, breathing information, skin/body temperature, brain activity, physical movement and/or lack of movement, information related to performance and/or non-performance of daily activities, activity duration information, physical pain information, and/or other physiological information. Examples of behavior information may include the subject demeanor, voice, look, gestures, manners, attitude, and/or other behavior information. Examples of medical information may include the subject's medical history, medications history, therapy history, coaching history, and/or other medical information related to the subject. Examples of psychological information may include the subject's personality, goals, intentions, preferences, beliefs, attitudes, emotions, perceptions, cognitions, and/or other psychological information related to the subject. In some embodiments, perception component 20 may be configured to obtain information related to the subject via input form the subject, a healthcare professional, and/or other users of system 10. In some embodiments, the information may be obtained via user interface 12. In some embodiments, perception component 20 may configured to control user interface 12 to present one or more views that facilitate entry and/or selection of information by the user. In some embodiments, the information may be obtained from other components within or outside system 10. For example, information may be transmitted to processors 18 from a remotely located database that is part of external resources 44, for example. In some embodiments, perception component 20 may be configured to obtain information related to other users that can apply to this user. For example, users in the same age group, same gender, users with similarities in their physiological, behavior, psychological, and/or medical information, and/or other users with other similarities to the user.

In some embodiments, perception component 20 may obtain information from a database, sensors 14, and/or other resources by electronically querying and/or requesting information from such devices and receiving the information in response. It should be noted that these examples are not intended to be limiting. Perception component 20 and/or processors 18 may be configured to receive and/or obtain information related to the subject, information from the sensors, and/or any other information in any way that allows system 10 to function as described herein.

Figure 2:
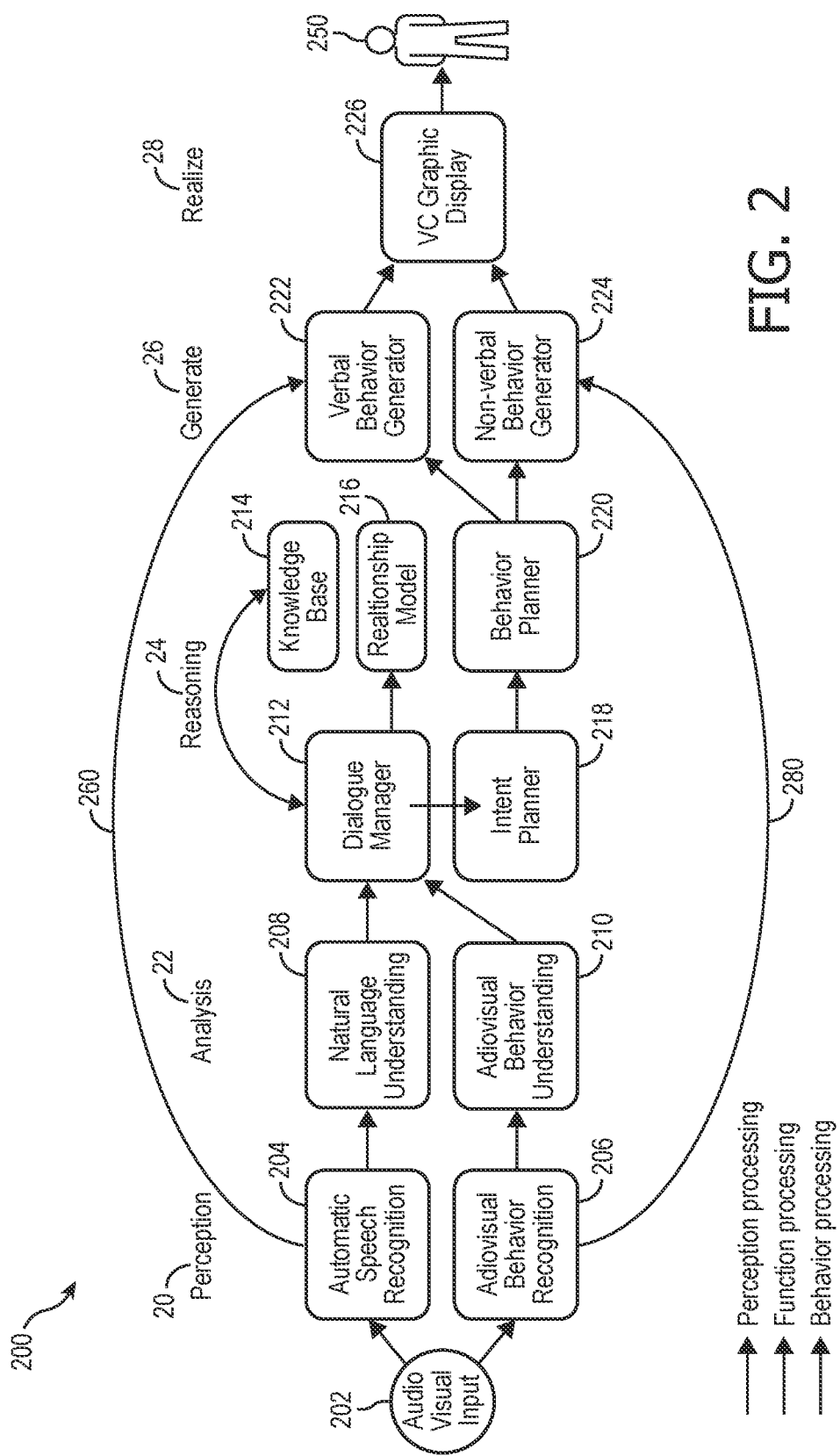
FIG. 2 illustrates an example of system architecture of the system in accordance with one or more implementations.

FIG. 2 illustrates an example of system architecture for system 10 in accordance with one or more implementations. In the example shown in FIG. 2, perception component 20 is configured to extract information related to the subject from the output signals, via automatic speech recognition 204 and/or audiovisual behavior recognition 206. In some embodiments, perception component may be configured to receive information through input from the user (e.g., typed input, multiple choice input, etc.). Perception component may be configured to extract information from audiovisual input 202 (e.g., the subject voice and/or video received from a microphone, and/or camera). Automatic speech recognition 204 may include identifying words and phrases in the subject speech and converting them into machine readable format. Audiovisual behavior recognition 206 may include facial recognition, body language recognition, recognition of acoustic non-content properties of speech (e.g., rhythm, emphasis, intonation, pitch, intensity, rate, etc.), and/or other behavior. In some embodiments, automatic speech and audiovisual behavior recognition may be achieved by using techniques such as hidden Markov models (HMM), Bayesian networks, neural network models, deep neural network models, reinforcement learning and/or other techniques of speech recognition and natural language processing.

Returning to FIG. 1, analysis component 22 is configured to determine a current state of the subject based on analysis of the information obtained from perception component 20. A current state of the subject may indicate an overall state of the subject health, mood, comfort, responsiveness, and/or other physical, physiological, and behavior states. In some embodiments, the current state of the subject may indicate one or more of a physiological state, a behavior state, and/or a medical state. For example, physiological, behavior, psychological, and/or medical states may be determined based on current information obtained by perception component 20 (e.g., information input by the subject, obtained from a subject database, obtained from a medical device related to the subject, obtained from sensors 14, etc.). In some embodiments, the current state of the subject may be a function of measured parameters (e.g., from sensors, and/or medical devices), and non-measured parameters (e.g., the subject answers to questions about how he feels, how he slept, if he has pain, etc.). In some embodiments, the current state of the subject may be a function of verbal and non-verbal parameters. Examples of verbal parameters may include information that the subject provides, via user interface 12, by saying the information, typing the information, selecting the information, and/or other methods of providing the information. Examples of non-verbal parameters may include parameters determined based on the subject demeanor, voice, look, gestures, manners, posture, attitude, etc.

By way of a non-limiting example, FIG. 2 shows an example of analysis component 22 configured to determine a current state of the subject from information extracted via automatic speech recognition and/or audiovisual recognition through natural language understanding techniques 208 and/or audiovisual behavior understanding techniques 210.

Returning to FIG. 1, reasoning component 24 is configured to determine a customized digital coaching plan for the subject. In some embodiments, the digital plan is dynamically customized as a result of interaction with the subject. For example, the agent can adapt in real-time and over time (within conversations, between multiple conversations) what he/she does and says in order to coach the subject. A digital coaching plan may include one or more of an electronic, and/or other coaching plans. In some embodiments, the customized digital coaching plan is based on the information related to the subject, the current state of the subject and/or other information. In some embodiment, the customized digital coaching plan may be based on information related to other users having similarities with the user. The customized digital coaching plan may include the type of coaching/advice to give the subject, the way in which the coaching/advice is given to the subject (based on his mood/responsiveness for example), the tone of voice to be used, the choice of words, gestures, the general demeanor, and/or other customization of the plan. In some embodiments, reasoning component 24 is configured to determine a relationship parameter that indicates the level of engagement of the subject with the adaptive embodied conversational agent. For example, the relationship parameter may be based on how often the user and agent interact, how the user reacts to advice, what emotions the user displays with respect to interaction with the embodied conversational agent, and/or other subject/embodied conversational agent relationship information.

FIG. 2 shows an example of reasoning component 24. Reasoning component 24 may include a dialogue manager 212, a knowledge base 214, a relationship model 216, an intent planner 218, a behavior planner 220, and /or other components. Dialogue manager 212 is configured to receive and analyze information related to the current state of the dialogue between the subject and the coach received from analysis component 22, information related to the subject received from knowledge base 214, and information related to the relationship parameter received from relationship model 216. In some embodiments, information related to the current state of the dialogue between the subject and the coach may be derived from one or more of information on the subject, previous conversations between the coach and the subject, and/or a model of how the conversation should develop. Analysis of information by dialogue manager 212 is provided to intent planner 218. Intent planner 218 is configured to determine the customized coaching plan for the subject based on the analysis of information and combined with the input from relationship model 216 and the input from the dialogue manager on the state of the dialogue. Behavior manager 220 is configured to determine the behavioral characteristics of the embodied conversational agent. For example emotional expressions, pitch, posture, movements, gestures, expressions, and/or other behavioral characteristics.

In some embodiments, knowledge base 214 includes information related to the subject that is provided by the subject, a user of system 10, and/or provided by other components of system 10, and information learned from previous interactions with the subject. Knowledge base 214 may be configured to learn from user input in real time, and dynamically update information in knowledge base 214. This may allow the embodied conversational agent to provide responses in real time (on-the-fly) based on new information (e.g., changes in the subject state and behavior over time, etc.). In some embodiments, perception component 20, analysis component 22, reasoning component 24, and/or other components of system are configured to dynamically adjust their analysis and output based on interaction with the subject in real or near real time.

Returning to FIG. 1, generation component 26 is configured to generate visual and/or audio signals conveying information related to the adaptive embodied conversational agent based on the customized digital coaching plan. The information related to the adaptive embodied conversational agent may include verbal behavioral characteristics and non-verbal characteristics of the adaptive embodied conversational agent. For example, the visual and/or audio signals generated include information about how the adaptive embodied conversational agent looks (when presented to the subject), how it moves, how it reacts to interaction with the subject, how it talks, the tone of the voice, the accent, the emotions expressed, and/or other information related to verbal behavioral characteristics and non-verbal characteristics of the adaptive embodied conversational agent.

FIG. 2 shows an example of generation component 26. Generation component 26 may include a verbal behavior generator 222, a non-verbal behavior generator 224, and/or other components. Verbal behavior generator 222 is configured to generate verbal behavior characteristics of the embodied conversational agent. For example, speech generation including features of the speech (e.g., tone, pitch, accent, emotion, etc.), content of the speech, and/or other verbal behavior characteristics of the embodied conversational agent. Non-verbal behavior generator 224 is configured to generate non-verbal behavior characteristics of the embodied conversational agent. For example, appearance of the embodied conversational agent, emotional expressions, movements, expressions, body language, posture, and/or other non-verbal behavior characteristics of the embodied conversational agent.

In some embodiments, generation component 26 is configured to generate visual and/or audio signals conveying information related to the adaptive embodied conversational agent based on an acceptance parameter. In some embodiment, an acceptance parameter may be determined by reasoning component 24 via relationship model 216 (described above). In some embodiments the acceptance parameter may be determined by other components within or outside of system 10. The acceptance parameter may indicate acceptance of the adaptive embodied conversational agent by the subject. Factors that may affect acceptance of the adaptive embodied conversational agent by the subject may include trust, likeability, perceived usefulness, and/or other factors. Acceptance of the embodied conversational agent by the subject may be important to delivering successful coaching. For example, if the subject does not trust, like, or see the value of interacting with the embodied conversational agent, the subject is unlikely to adhere to the advice provided by the embodied conversational agent, and unlikely to profit from the embodied conversational agent ability to provide continuous health management support over time.

In some embodiments, the acceptance parameter may be based on one or more of a similarity, a familiarity, and/or a realism parameter. For example, the similarity parameter may indicate how similar the embodied conversational agent is to the subject in age, ethnicity, gender, and/or other similarities between the embodied conversational agent and the subject. In some embodiments, the subject may be more receptive to advice received from someone he perceives to be similar to him. The familiarity parameter may indicate how familiar the embodied conversational agent is to the subject. For example, the subject may be more receptive to an embodied conversational agent that has characteristics such as appearance, communication style, and/or mannerisms similar to a trusted person (e.g., parent, sibling, nurse, etc.) that is known and trusted by the subject. The realism parameter may indicate how realistic the appearance of the embodied conversational agent is. For example, the subject may be more receptive to a virtual coach that has a more realistic appearance (looks like a human). In some embodiments, similarity, familiarity, and/or a realism parameters may influence each other and/or interactions between the parameters may occur.

In some embodiments, the embodied conversational agent may be adaptive based on the subject preferences. For example, some subjects may be more receptive to information provided by older-looking adults while other subjects may be more receptive to information provided by a younger-looking agent, yet other subjects may be more receptive to agents from the opposite gender, yet other subjects may be more receptive to a more stylized appearance (less realistic) In some embodiments, the subject may customize the embodied conversational agent via user interface 12. In some embodiments, generation component may be configured to adjust the appearance of the embodied conversational agent based on previous interactions with the subject and compliance of the subject with previous advice given by the embodied conversational agent.

Realization component 28 is configured to receive the generated visual and/or audio signals and cause presentation of the adaptive embodied conversational agent on display 16 to provide the customized digital coaching plan to the subject interactively. The customized digital coaching plan is presented to the subject via the embodied conversational agent which interacts with the subject in verbal (speech) manners and non-verbal (emotional expressions, facial expressions, body movement, etc.). In some embodiments, realization component may be included in display 16. Examples of display 16 may include subject monitors, nursing stations, mobile communications devices, subject information systems, and/or other graphic or electronic displays. FIG. 2 shows an example of realization component 28 including a graphic display 226. Graphic display is configured to receive the generated signals and generate embodied conversational agent 250.

In some embodiments, the embodied conversational agent may be generated dynamically in real or near-real time in response to interaction with the subject. In some embodiments, the embodied conversational agent may be generated dynamically in real or near-real time based on output of perception component 20 only without analysis component 22, and reasoning component 24. Arrows 260 and 280 in FIG. 2 show the process by which generation component 26 receives information directly from perception component 20 and generates verbal and non-verbal characteristics of embodied conversational agent 250 to be realized and displayed by realization component 28. This may allow embodied conversational agent 250 to provide quick responses to the user without analysis and planning.

In operation, in some embodiments, the embodied conversational agent may be integrated with one or more medical, monitoring devices, and/or other coaching system in an in-home care system (e.g., Philips digital environment eCareCompanion (eCP)). In this example, the embodied conversational agent may be used with a tablet-based interface. This interface enables subject to manually enter measurements and respond to survey questions. The embodied conversational agent may provide the subjects with feedback on how their measurements (e.g., blood pressure, weight, etc.) changed over time, assist the subject in using the one or more medical and/or monitoring devices, assist the subject in entering physiological measurements, assist the subject in filling out surveys, schedule appointments, provide reminder to the subject of upcoming appointments, and/or may provide other assistance to the subject.

In some embodiments, the embodied conversational agent may be configured to support user-initiated and/or system-initiated interactions. For example, the embodied conversational agent may be configured to send personalized messages to the subject, providing him or her pro-actively with information updates, reminders, questions, and/or other interactions initiated by the embodied conversational agent. In some embodiments, the embodied conversational agent may be configured to support the subject responsive to the subject request. For example, the embodied conversational agent may provide assistance if the subject requests help preparing for a meeting with a physician, or when he/she feels lonely. The embodied conversational agent may provide assistance to the subject based on the subject's request, information related to the subject and information about the subject's state based on visual cues and speech from the subject. In some embodiments, the embodied conversational agent is configured to provide long-term support to the subject. For example, the embodied conversational agent may support the subject through monitoring behavior changes and providing guidance to the subject through the changes which may create a social bond with the subject based on trust and believability.

The architecture shown in FIG. 2 is designed to be compliant to the SAIBA framework (Situation, Agent, Intention, Behavior, Animation). Such framework defines modular structure, functionalities and communication protocols for system 10. At the base of this approach is a separation between the perception process (which specifies perceived nonverbal behaviors of the user), the functional process (which provide information about the user's intent, functional role or affective state of the user behavior) and the behavior process (which specifies verbal and nonverbal behaviors of the agent). These specifications can be implemented by the semantic structures of the Perception Markup Language (PML), the Functional Markup Language (FML), and the Behavioral Markup Language (BML), respectively.

Figure 3:
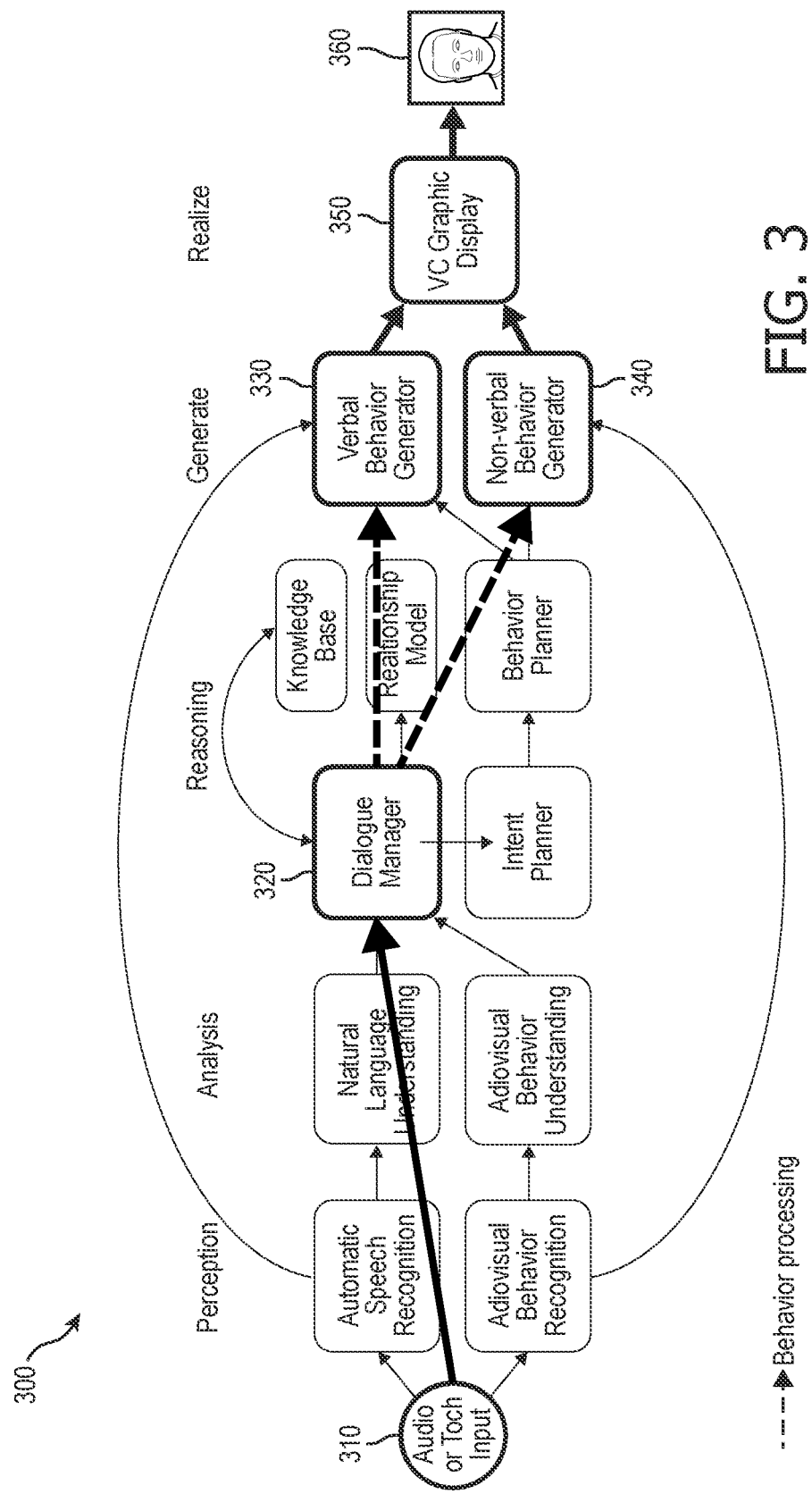
FIG. 3 illustrates an example diagram of operations of the system in accordance with one or more implementations.

FIG. 3 illustrates an example 300 of an embodied conversational agent 360 configured as a reminder system. The embodied conversational agent is configured as a reminder system to remind subjects of taking their measurements or filling out surveys, and guiding them through the procedures to do so. Dialogue manager 320 receives audio or touch input 310 from the subject. Embodied conversational agent 360 is generated and displayed by graphic display 350 based on verbal and non-verbal behavior of the embodied conversational agent generated by verbal behavior generator 330, and non-verbal behavior generator 340. In this embodiment, CrazyTalk software was used for the implementation of the appearance of embodied conversational agent 360 for its flexibility and customization of the appearance and behavior of the embodied conversational agent. Embodied conversational agent 360 was generated deployed on Android, using the Unity platform to create the interactive user experience. Other software and platforms may be used.

FIG. 4 illustrates features of system 10 in accordance with one or more embodiments. Interaction features 410 describe different features of interaction between the user and system 10. For example, interaction features may include touch screen input, typed input, speech recognition, user controlled settings, user non-verbal behavior recognition, context recognition, interruption mechanisms, user initiated conversation, agent initiated conversation, and/or other features of interaction between the user and system 10. Speech production features 420 describe the features of the agent speech production. For example, speech production features may include pre-recorded speech, generated synthetic speech, synchronization with animation, variability in content expression, variability in intonation, variability of discourse patterns, features of the agent speech (pitch, accent, emotions, etc.), and/or other agent speech production features. Intelligence features 430 describe intelligence features of the agent. For example, these features may include consistency, coherence, clear conversation, dynamic conversation based on user input and based on information from other sources (data from other medical devices, knowledge base, medical history, past interactions with the user, etc.). Appearance features 440 describe features of the agent appearance. Such features may include 2+D rendering, using a real person picture, emotional expressions, movement of head, posture, variability in expressions, background, handling objects, body movement, and/or other agent appearance features.

Electronic storage 40 comprises electronic storage media that electronically stores information. The electronic storage media of electronic storage 40 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 40 may be (in whole or in part) a separate component within system 10, or electronic storage 40 may be provided (in whole or in part) integrally with one or more other components of system 10 (e.g., user interface 12, processor 18, etc.). In some embodiments, electronic storage may be located in a server together with processor 18, in a server that is part of external resources 44, in a computing device associated with the user and/or other users, and/or in other locations. Electronic storage 40 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 40 may store software algorithms, information determined by processor 18, information received via user interface 12 and/or external computing systems, information received from external resources 44, information received from sensors 14, and/or other information that enables system 10 to function as described herein.

It is to be understood that other communication techniques, either hard-wired or wireless, are also contemplated by the present disclosure as user interface 12. For example, the present disclosure contemplates that user interface 12 may be integrated with a removable storage interface provided by electronic storage 40. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 12 comprise, but are not limited to, an RS-232 port, RF link, an IR link, modem (telephone, cable or other). In short, any technique for communicating information with system 10 is contemplated by the present disclosure as user interface 12.

External resources 44 may include sources of information (e.g., databases, websites, etc.), external entities participating with system 10 (e.g., a medical records system of a health care provider), medical equipment configured to communicate with external systems, one or more servers outside of system 10, a network (e.g., the internet), electronic storage, equipment related to Wi-Fi technology, equipment related to Bluetooth® technology, data entry devices, sensors, scanners, computing devices associated with individual users, and/or other resources. In some implementations, some or all of the functionality attributed herein to external resources 44 may be provided by resources included in system 10. External resources 44 may be configured to communicate with sensors 14, processor 18, electronic storage 40, user interface 12, and/or other components of system 10 via wired and/or wireless connections, via a network (e.g., a local area network and/or the internet), via cellular technology, via Wi-Fi technology, and/or via other resources.

Network 50 may include the Internet and/or other networks, Intranets, a PAN (Personal Area Network), a LAN (Local Area Network), a WAN (Wide Area Network), a SAN (Storage Area Network), a MAN (Metropolitan Area Network), near field communication, frequency (RF) link, Bluetooth, Wi-Fi, Li-FI, a cellular communications network, a Public Switched Telephone Network, and/or any type(s) of wired or wireless network(s). It will be appreciated that this is not intended to be limiting and that the scope of this disclosure includes embodiments in which the components of system 10 are operatively linked via some other communication media. In some cases, the network is a secure local area network, such as a wired Ethernet network behind a firewall.

Figure 5:
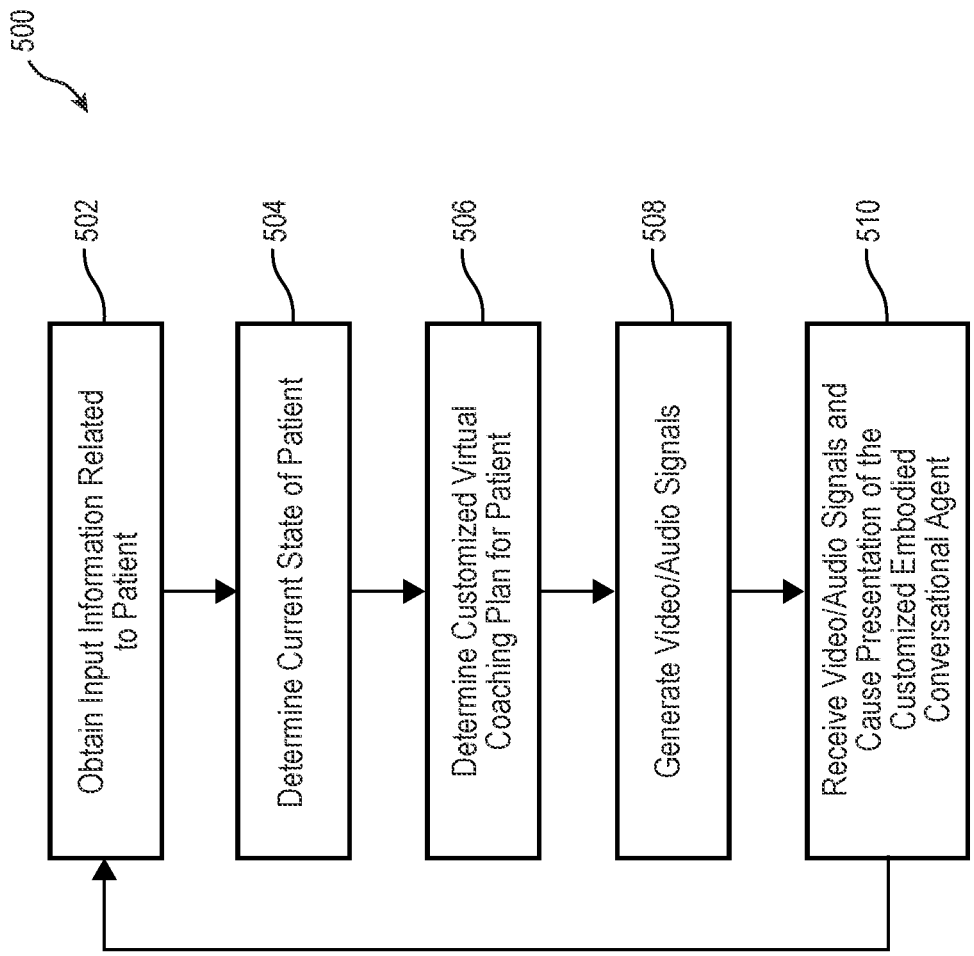
FIG. 5 illustrates a method for generating an adaptive embodied conversational agent to provide interactive virtual coaching to a subject, in accordance with one or more implementations.

FIG. 5 illustrates a method 500 for generating a adaptive embodied conversational agent to provide interactive virtual coaching to a medical subject. The system comprises a user interface, one or more hardware processors, a display, and/or other components. The one or more hardware processors are configured to execute computer program components. The computer program components comprise a perception component, an analysis component, a reasoning component, a generation component, a realization component and/or other components. The operations of method 500 presented below are intended to be illustrative. In some embodiments, method 500 may be accomplished with one or more additional operations not described, and/or without one or more of the operations discussed. Additionally, the order in which the operations of method 500 are illustrated in FIG. 5 and described below is not intended to be limiting.

In some embodiments, method 500 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 500 in response to instructions stored electronically on an electronic storage medium. The one or more processing devices may include one or more devices configured through hardware, firmware, and/or software to be specifically designed for execution of one or more of the operations of method 500.

At an operation 502, input information related to the subject is obtained. The information may include one or more of physiological information, behavior information, and/or medical information. In some embodiments, input information may be obtained from a user interface. In some embodiments, operation 502 is performed by a processor component the same as or similar to perception component 20 (shown in FIG. 1 and described herein).

At an operation 504, a current state of the subject is determined based on analysis of the information obtained at operation 502. In some embodiments, the current state indicates one or more of a physiological state, a behavior state, and/or a medical state. In some embodiments, operation 504 is performed by a processor component the same as or similar to analysis component 22 (shown in FIG. 1 and described herein).

At an operation 506, a customized digital coaching plan for the subject is determined or adjusted. In some embodiments, the customized digital coaching plan may be based on the information related to the subject, the current state of the subject, and/or other information. In some embodiments, operation 506 is performed by a processor component the same as or similar to reasoning component 24 (shown in FIG. 1 and described herein).

At an operation 508 visual and/or audio signal conveying information related to the adaptive embodied conversational agent is generated based on the customized digital coaching plan. In some embodiments, the information related to the adaptive embodied conversational agent includes verbal behavioral characteristics and non-verbal characteristics of the adaptive embodied conversational agent. In some embodiments, operation 508 is performed by a processor component the same as or similar to generation component 26 (shown in FIG. 1 and described herein).

At an operation 510 the generated visual and/or audio signals is received causing presentation of the adaptive embodied conversational agent on the display to provide the customized digital coaching plan to the subject interactively. In some embodiments, operation 510 is performed by a processor component the same as or similar to realization component 28 (shown in FIG. 1 and described herein). In some embodiments, operations 502-510 described above are reiterated in a feedback loop manner from 510 to 502 in a continuous process (e.g.,getting input, adapting, giving output, getting input, etc.)

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to generate an adaptive embodied conversational agent, the adaptive embodied conversational agent being configured to provide interactive virtual coaching to a subject, the system comprising:
   a user interface, configured to obtain input information related to the subject, wherein the information includes one or more of physiological information, behavior information, psychological information, and/or medical information;
one or more hardware processors configured by machine-readable instructions to:
determine a customized digital coaching plan for the subject, wherein the customized digital coaching plan is based on the information related to the subject;
generate visual and/or audio signals conveying information related to the adaptive embodied conversational agent based on the customized digital coaching plan, wherein the information related to the adaptive embodied conversational agent includes verbal behavioral characteristics and non-verbal characteristics of the adaptive embodied conversational agent;
determine a relationship parameter, the relationship parameter indicating the status of the relationship between the subject and the adaptive embodied conversational agent, and wherein determining the customized digital coaching plan is further based on the relationship parameter; and
a display configured to receive the generated visual and/or audio signals and cause presentation of the adaptive embodied conversational agent on the display to provide the customized digital coaching plan to the subject interactively.

2. The system of claim 1, wherein the one or more hardware processors are further configured to determine a current state of the subject based on analysis of information obtained by the user interface, the current state indicating one or more of a physiological state, a behavior state, psychological state, and/or a medical state, and wherein determining the customized digital coaching plan is based on the current state of the subject.

3. The system of claim 1, wherein the user interface includes one or more sensors configured to generate output signals conveying information related to verbal and non-verbal behavior of the subject, wherein the one or more hardware processors are further configured to extract information related to the subject from the output signals.

4. The system of claim 3, wherein the one or more sensors include one or more of physiological sensors, audio sensors, and/or visual sensors.

5. The system of claim 1, wherein the one or more hardware processors are further configured to determine an acceptance parameter, the acceptance parameter indicating acceptance of the adaptive embodied conversational agent by the subject, and wherein generating the embodied conversational agent is based on the acceptance parameter.

6. The system of claim 1, wherein the verbal and non-verbal characteristics of the adaptive embodied conversational agent are adjusted based on interaction with the subject.

7. A method for generating an adaptive embodied conversational agent, the adaptive embodied conversational agent being configured to provide interactive virtual coaching to a subject with a system comprising a user interface, one or more hardware processors, and a display; the method comprising:
obtaining, with the user interface, input information related to the subject, wherein the information includes one or more of physiological information, behavior information, psychological information, or medical information;
determining, with the one or more hardware processors, a customized digital coaching plan for the subject, wherein the customized digital coaching plan is based on the information related to the subject;
generating, with the one or more hardware processors, visual and/or audio signals conveying information related to the adaptive embodied conversational agent based on the customized digital coaching plan, wherein the information related to the adaptive embodied conversational agent includes verbal behavioral characteristics and non-verbal characteristics of the adaptive embodied conversational agent;
determining, with the one or more hardware processors, a relationship parameter, the relationship parameter indicating the status of the relationship between the subject and the adaptive embodied conversational agent, and wherein determining the customized digital coaching plan is further based on the relationship parameter; and
receiving, with the display, the generated visual and/or audio signals and causing presentation of the adaptive embodied conversational agent on the display to provide the customized digital coaching plan to the subject interactively.

8. The method of claim 7, further comprising determining, with the one or more hardware processors, a current state of the subject based on analysis of the information obtained by the user interface, the current state indicating one or more of a physiological state, a behavior state, and/or a medical state, and wherein determining the customized digital coaching plan is based on the current state of the subject.

9. The method of claim 7, wherein the user interface includes one or more sensors configured to generate output signals conveying information related to verbal and non-verbal behavior of the subject, and wherein the method further comprises:
extracting, with the one or more hardware processors, information related to the subject from the output signals.

10. The method of claim 9, wherein the one or more sensors include one or more of physiological sensors, audio sensors, or optical sensors.

11. The method of claim 7, further comprising determining, with the one or more hardware processors, an acceptance parameter, the acceptance parameter indicating acceptance of the adaptive embodied conversational agent by the subject, and wherein generating the embodied conversational agent is based on the acceptance parameter.

12. The method of claim 7, further comprising adjusting the verbal and non-verbal characteristics of the adaptive embodied conversational agent based on interaction with the subject.

13. A system configured to generate an adaptive embodied conversational agent, the adaptive embodied conversational agent being configured to provide interactive virtual coaching to a subject, the system comprising:
means for obtaining input information related to the subject, wherein the information includes one or more of physiological information, behavior information, psychological information, and/or medical information;
means for determining a customized digital coaching plan for the subject, wherein the customized digital coaching plan is based on the information related to the subject;
means for generating visual and/or audio signals conveying information related to the adaptive embodied conversational agent based on the customized digital coaching plan, wherein the information related to the adaptive embodied conversational agent includes verbal behavioral characteristics and non-verbal characteristics of the adaptive embodied conversational agent;

means for determining a relationship parameter, the relationship parameter indicating the status of the relationship between the subject and the adaptive embodied conversational agent, and wherein determining the customized digital coaching plan is further based on the relationship parameter; and means for receiving the generated visual and/or audio signals and causing presentation of the adaptive embodied conversational agent on the display to provide the customized digital coaching plan to the subject interactively.

14. The system of claim 13, further comprising means for determining a current state of the subject based on analysis of the information obtained from the user interface, the current state indicating one or more of a physiological state, a behavior state, psychological state, and/or a medical state, and wherein determining the customized digital coaching plan is based on the current state of the subject.

15. The system of claim 14, wherein the means for obtaining input information include one or more sensors configured to generate output signals conveying information related to verbal and non-verbal behavior of the subject, and the system further comprises means for extracting information related to the subject from the output signals.

16. The system of claim 15, wherein the one or more sensors include one or more of physiological sensors, audio sensors, and/or optical sensors.

17. The system of claim 14, further comprising means for determining an acceptance parameter, the acceptance parameter indicating acceptance of the adaptive embodied conversational agent by the subject, and wherein generating the embodied conversational agent is based on the acceptance parameter.

18. The system of claim 14, further comprising means for adjusting the verbal and non-verbal characteristics of the adaptive embodied conversational agent based on interaction with the subject.

* * * * *